(12) United States Patent
Yelle

(10) Patent No.: US 7,098,224 B2
(45) Date of Patent: Aug. 29, 2006

(54) HYDROXYLANSOPRAZOLE METHODS

(75) Inventor: William E. Yelle, Billerica, MA (US)

(73) Assignee: Sepracor Inc., Marlborough, MA (US)

( * ) Notice: Subject to any disclaimer, the term of this patent is extended or adjusted under 35 U.S.C. 154(b) by 195 days.

(21) Appl. No.: 10/685,628

(22) Filed: Oct. 14, 2003

(65) Prior Publication Data

US 2004/0077688 A1    Apr. 22, 2004

Related U.S. Application Data

(60) Continuation of application No. 10/046,464, filed on Oct. 19, 2001, now abandoned, which is a division of application No. 09/357,458, filed on Jul. 20, 1999, now Pat. No. 6,335,351.

(60) Provisional application No. 60/093,762, filed on Jul. 22, 1998.

(51) Int. Cl.
*A61K 31/44* (2006.01)
(52) U.S. Cl. .................................................. 514/338
(58) Field of Classification Search ............... None
See application file for complete search history.

(56) References Cited

U.S. PATENT DOCUMENTS

| 4,628,098 A | 12/1986 | Nohara et al. ............... 546/271 |
| 4,689,333 A | 8/1987 | Nohara et al. ............... 514/338 |

OTHER PUBLICATIONS

HCAPLUS DN 123:132521, Fort F et al.*
HCAPLUS DN 115:21996, Inatomi N et al, Yakuri to Chiryo, 1991, 19(2) 477-86, abstract.*
JICST-Eplus AN 961013832, Nakamura K et al, J clin Ther Med, 1996 12 (13) 2775-2788, abstract.*

Katsuki et al. "Determination of R(+)-and S(−)-Lansoprazole Using Chiral Stationary-Phase Liquid Chromatography . . . " *Pharm. Res.* 13, 611-615 (1996).
Pearce et al. "Identification of the Human P450 Enzymes Involved in Lansoprazole Metabolism" *J. Pharm. Exp. Ther.* 277, 805-816 (1996).
Fort et al. "Mechanism for Species-Specific Induction of Leydig Cell Tumors in Rats by Lansoprazole" *Fund. Appl. Toxicol.* 26, 191-202 (1995).
Andersson "Pharmacokinetics, Metabolism and Interactions of Acid Pump Inhibitors" *Clin. Pharmacokinet 1*, 9-28 (1996).
Chem. Abstract 115:21996.
Katsuki et al. "Genetic polymorphism of CYP2C19 and lansoprazole pharmacokinetics in Japanese subjects" *Eur. J. Clin. Pharmacol.* 52, 391-396 (1997).
Nagata et al. "Growth Inhibition of *Ureaplasma Urealyticum* by the Proton Pump Inhibitor Lansoprazole: Direct Attribution to Inhibition . . . " *Anti, Agents Chemo. 39*, 2187-2192 (1995).
Sohn et al. "Metabolic disposition of lansoprazole in relation to the S-mephenytoin 4'-hdroxylation phenotype status" *Clin. Pharm. Ther, 61*, 574-582 (1997).
Pichard et al. "Oxidative Metabolism of Lansoprazole by Human Liver Cytochromes P450" *Mol. Pharm. 47*, 410-418 (1995).
Aoki et al. "High-performance liquid chromatographic determination of lansoprazole and its metabolites in human serum and urine" *J. Chromatography 571*, 283-290 (1991).

* cited by examiner

*Primary Examiner*—Dwayne C. Jones
(74) *Attorney, Agent, or Firm*—Heslin Rothenberg Farley & Mesiti P.C.

(57) ABSTRACT

Methods and compositions are disclosed utilizing hydroxylansoprazole for the treatment of ulcers in humans. Hydroxylansoprazole exhibits a lessened liability toward drug-drug interactions than lansoprazole and a more predictable dosing regimen than lansoprazole. Hydroxylansoprazole is also useful for the treatment of gastroesophageal reflux and other conditions related to gastric hypersecretion such as Zollinger-Ellison Syndrome.

13 Claims, No Drawings

HYDROXYLANSOPRAZOLE METHODS

CROSS REFERENCE TO RELATED APPLICATIONS

This application is a continuation of U.S. application Ser. No. 10/046,464, filed Oct. 19, 2001 now abandoned, which is a divisional of U.S. application Ser. No. 09/357,458, filed Jul. 20, 1999, now U.S. Pat. No. 6,335,351, which claimed the priority of provisional application No. 60/093,762, filed Jul. 22, 1998. The entire disclosures of all are incorporated herein by reference.

FIELD OF THE INVENTION

This invention relates to compositions of matter containing hydroxylansoprazole. The invention also relates to methods of treating and preventing ulcers, treating other conditions related to gastric hypersecretion, and treating psoriasis.

BACKGROUND OF THE INVENTION

Lansoprazole I is an orally active, potent,

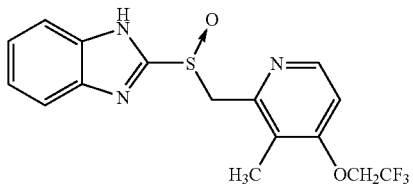

irreversible inhibitor of $H^+,K^+$-ATPase. It is commercially available in the form of Prevacid® delayed release capsules from TAP Pharmaceuticals Inc. The compound is one of the class of compounds known as gastric "proton pump" inhibitors. These compounds are weak organic bases which diffuse passively from the plasma into the acid-containing intracellular canaliculi of gastric parietal cells. At the low pH found in the lumen of these canaliculi, the protonated compounds rearrange to form pyridinium sulfenamides, which react with sulfhydryl groups present on the ATPase localized in the membranes lining the intracellular canaliculi. The alkylation of the sulfhydryl inhibits the ability of the enzyme to catalyze the secretion of $H^+$ into the lumen in exchange for $K^+$ ions. This inhibition results in an overall reduction in hydrochloric acid secretion by the parietal cells into the cavity of the stomach, thus increasing intragastric pH. As a consequence of reduced acidity in the stomach, the activity of the proteolytic enzyme pepsin is also markedly decreased. Because the proton pump is the final step in acid production and the compounds of this class combine covalently with the associated $H^+,K^+$-ATPase, a profound and prolonged inhibition of gastric acid secretion can be achieved.

Proton pump inhibitors have also been reported as useful in treating psoriasis. [See PCT application WO95/18612] The $C_{max}$ of racemic lansoprazole is at about 1.5 to 3.5 hours in humans after administration of enteric-coated granules, and the serum half-life is about 1 to 3 hours, although this is variable, depending on the subject=s age and liver function, as discussed below. The major metabolites in human serum are 5-hydroxylansoprazole II (referred to as hydroxylansoprazole herein) and lansoprazole sulfone III.

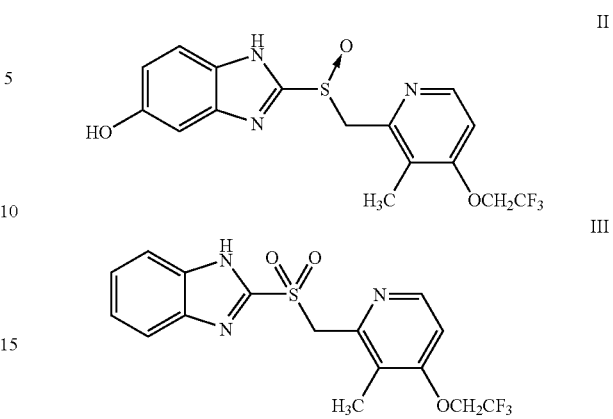

The two major primary metabolites, lansoprazole sulfone and 5-hydroxylansoprazole, are formed by cytochromes P450 3A (CYP3A) and 2C19 (CYP2C19), respectively. Both metabolites undergo further metabolism to the common metabolite 5-hydroxylansoprazole sulfone via CYP2C19 and CYP3A, respectively. Thus, both CYP enzymes are sequentially—but alternatively—involved in lansoprazole metabolism. CYP2C19, the S-mephenytoin hydroxylase, is polymorphically expressed in the human population. The mutant allele constitutes the recessive trait. Homozygous carriers of the mutation completely lack CYP2C19 and are referred to as poor metabolizers (PM's); persons homozygous and heterozygous for the "normal" allele are extensive metabolizers (EM's). A hereditary deficiency of the alternative enzyme, CYP3A, has not been demonstrated in the human population.

It would be desirable to find a compound with the advantages of lansoprazole which would provide a more predictable dosage regimen in the patient population and that would decrease the chances for drug-drug interactions.

SUMMARY OF THE INVENTION

This invention relates to the use of hydroxylansoprazole for treating ulcers of the stomach, duodenum and esophagus, gastroesophageal reflux diseases, Zollinger-Ellison Syndrome, and other disorders including those that would benefit from an inhibitory action on gastric acid secretion. Hydroxylansoprazole inhibits the $H^+, K^+$-ATPase associated with the gastric proton pump and the resulting secretion of gastric acid by parietal cells providing therapy in diseases associated with gastric hyperacidity. The invention also relates to a method of treating psoriasis using hydroxylansoprazole. Hydroxylansoprazole provides a more predictable dosage regimen in the patient population and decreases the chances for drug-drug interactions by avoiding oxidative metabolism for which the cytochrome P450 2C19 enzyme system is required.

The invention also relates to certain pharmaceutical compositions containing hydroxylansoprazole.

DETAILED DESCRIPTION OF THE INVENTION

The active compound of these compositions and methods is hydroxylansoprazole. Racemic hydroxylansoprazole may be prepared using methods well known to those skilled in the art, e.g. by a modification of the method described in U.S.

Pat. Nos. 4,628,098 and 4,689,333. The compound identified in these patents as intermediate II

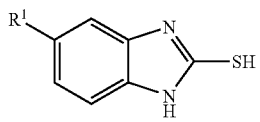

is provided with a substituent R¹=methoxymethyl (MOM) by treatment of the corresponding hydroxy compound with dimethoxymethane (formaldehyde dimethyl acetal) in the presence of an acid catalyst (e.g. TsOH) and molecular sieves. Following condensation with the hydroxymethylpyridine III of the patents, and before oxidation, the MOM protecting group is cleaved with HCl in isopropanol/THF. Throughout this application, various references are referred to, often, although not always, within parentheses or square brackets. The disclosures of all of these publications in their entireties are hereby incorporated by reference as if written herein.

The index name for hydroxylansoprazole (II) in Chemical Abstracts is 2[[[3-methyl-4-(2,2,2-trifluoroethoxy)-2-pyridinyl]methyl]sulfinyl]-1 H-benzimidazol-5-ol; it is also known as 5-hydroxy-2-[3-methyl-4-(2,2,2-trifluoroethoxy)pyrid-2-yl]methyl-sulfinylbenzimidazole. The registry number of racemic hydroxylansoprazole is 131926-998-2.

Hydroxylansoprazole possesses a center of asymmetry at the sulfoxide sulfur, giving rise to two enantiomers. Throughout the instant disclosure, when the term is not otherwise modified, hydroxylansoprazole includes the (+) enantiomer, the (−) enantiomer and any mixture of the two. The preparation of the individual enantiomers of the parent, lansoprazole, has been described in the literature, but the enantiomers of hydroxylansoprazole have not been previously disclosed. The individual enantiomers of hydroxylansoprazole can be obtained using methods well known to those skilled in the art, e.g. by asymmetric oxidation of the thioether precursor, or by achiral oxidation of the thioether precursor followed by separation of the enantiomers, e.g. by bioreduction of the racemate to eliminate one or the other enantiomer in analogous fashion to the procedure described for lansoprazole in PCT applications WO 9602535 and 9617077.

Inatomi et al. [Yakuri to Chiryo 19, 477–486 (1991); Chem. Abst. 115:21996] have indicated that although the parent lansoprazole inhibited acid formation in isolated parietal cells with an $IC_{50}$ of 0.09 μM, racemic hydroxylansoprazole did not inhibit acid formation in isolated parietal cells.

It has now been discovered that hydroxylansoprazole is a superior agent for treating ulcers of the stomach, duodenum and esophagus, gastroesophageal reflux diseases, Zollinger-Ellison Syndrome, psoriasis and other disorders, including those that would benefit from an inhibitory action on $H^+,K^+$-ATPase in that it provides this effective treatment while exhibiting fewer or less severe adverse effects than lansoprazole, less potential for drug-drug interactions than lansoprazole and a more predictable dosing regimen than lansoprazole. Adverse effects of lansoprazole include hepatocellular neoplasia, gastric carcinoids, headache, diarrhea and skin alterations.

The present invention encompasses a method of treating ulcers, which comprises administering to a human in need of such therapy, an amount of hydroxylansoprazole, or a pharmaceutically acceptable salt thereof, sufficient to alleviate the symptoms of ulcers. The present invention also encompasses an oral antiulcer composition for the treatment of a human in need of antiulcer therapy, which comprises a pharmaceutically acceptable carrier for oral administration and a therapeutically effective amount of hydroxylansoprazole or a pharmaceutically acceptable salt thereof. Preferably the composition is in the form of a tablet or capsule, and the amount of hydroxylansoprazole in the tablet or capsule is preferably about between 100 and 500 mg. The present invention further encompasses a method of treating gastroesophageal reflux disease and of treating conditions caused by or contributed to by gastric hypersecretion. Conditions associated with hypersecretion in humans may include, but are not limited to, Zollinger-Ellison syndrome. The present invention further encompasses a method of treating psoriasis.

Utilizing hydroxylansoprazole results in enhanced dosage predictability and an improved therapeutic index. In particular, hydroxylansoprazole exhibits less variation in the patient population between so-called extensive metabolizers and poor metabolizers than does lansoprazole.

The term "treating ulcers" as used herein means treating, alleviating or palliating such conditions, and thus providing relief from the symptoms of nausea, heartburn, post-prandial pain, vomiting, and diarrhea. The term "a method for treating gastroesophageal reflux diseases in a human" as used herein means treating, alleviating or palliating the conditions that result from the backward flow of the stomach contents into the esophagus. The term "treating a condition caused, or contributed to, by gastric hypersecretion in a human" as used herein means treating, alleviating or palliating such disorders associated with hypersecretion, thus providing relief from the symptoms of the aforementioned conditions. Zollinger-Ellison Syndrome is among the conditions caused by or contributed to by hypersecretion. The term "treating psoriasis" as used herein means treating, alleviating or palliating the condition, and thus providing relief from the symptoms of pruritis, epidermal scaling, itching and burning.

The term Aoptically pure@ as used herein means that the compositions contain at least 90% by weight of one enantiomer and 10% by weight or less of the other. In a more preferred embodiment the term "substantially optically pure" means that the composition contains at least 99% by weight of one enantiomer, and 1% or less of the opposite enantiomer. In the most preferred embodiment, the term "substantially optically pure" as used herein means that the composition contains greater than 99% by weight of a single enantiomer. These percentages are based upon the total amount of hydroxyomeprazole in the composition.

The magnitude of a prophylactic or therapeutic dose of hydroxylansoprazole in the acute or chronic management of disease will vary with the severity of the condition to be treated and the route of administration. The dose and perhaps the dose frequency will also vary according to the age, body weight and response of the individual patient. In general, the total daily dose range for hydroxylansoprazole for the conditions described herein is from about 50 mg to about 1500 mg in single or divided doses. Preferably a daily dose range should be about 500 mg to about 1000 mg in single or divided doses. In managing the patient, the therapy should be initiated at a lower dose, perhaps at about 50 mg and increased up to about 1000 mg or higher depending on the patient's global response. It is further recommended that children and patients over 65 years and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The terms "an amount sufficient to alleviate or palliate ulcers" "an amount sufficient to alleviate the symptoms of gastroesophageal reflux", "an amount sufficient to alleviate gastric hypersecretion" and Aan amount sufficient to treat psoriasis@ are encompassed by the above-described dosage amounts and dose frequency schedule.

The relative activity, potency and specificity of hydroxylansoprazole both as a gastric antisecretory agent and as a plasma gastrin elevating agent can be determined by a pharmacological study in animals according to the method of Decktor et al. [*J. Pharmacol. Exp. Ther.* 249, 1–5 (1989)]. The test provides an estimate of relative activity, potency and, through a measure of specificity, an estimate of therapeutic index. Fasted rats, implanted with a gastric cannula, receive single oral or parenteral doses of (+) hydroxylansoprazole, (–) hydroxylansoprazole or racemate, 1 hour before collection of gastric juice over a four hour period. Acid output and pH are then determined on each sample. Dose response evaluations are performed with each compound to determine the lowest dose which inhibits acid output by at least 95% and maintains gastric pH above 7.0. Plasma gastrin levels are then determined in a second group of rats treated with the doses selected in the first series of tests. Blood samples are taken for analyses over the five hour period after dosing, and both peak level as well as area-under-the-curve analyses of the gastrin responses are made. These responses are then analyzed statistically using Student's "t" test to assess whether equivalent antisecretory doses show differences in gastrin responses.

Any suitable route of administration may be employed for providing the patient with an effective dosage of hydroxylansoprazole. Rectal, parenteral (subcutaneous, intramuscular, intravenous), transdermal, and like forms of administration are possible, but oral administration is preferred. Oral dosage forms include tablets, troches, dispersions, suspensions, solutions, capsules, and the like.

The pharmaceutical compositions of the present invention comprise hydroxylansoprazole as the active ingredient, or a pharmaceutically acceptable salt thereof, and may also contain a pharmaceutically acceptable carrier, and optionally, other therapeutic ingredients. The terms "pharmaceutically acceptable salts" or "a pharmaceutically acceptable salt thereof" refer to salts prepared from pharmaceutically acceptable non-toxic bases. Since the compound of the present invention is a weak acid and is unstable at low pH, salts may be prepared from pharmaceutically acceptable non-toxic bases including inorganic and organic bases. Suitable pharmaceutically acceptable base addition salts for the compound of the present invention include metallic salts of aluminum, calcium, lithium, magnesium, potassium, sodium, titanium and zinc or organic salts made from lysine, N,N'-dibenzylethylenediamine, chloroprocaine, choline, diethanolamine, ethylenediamine, meglumine (N-methylglucamine) and procaine. Sodium salts are preferred.

The compositions of the present invention include suspensions, solutions, elixirs or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. It has been found that the inclusion of mannitol and of basic salts of calcium and magnesium in the compositions allows the preparation of tablets and capsules that retain good stability. Because of the acid instability of hydroxylansoprazole, it is usually advantageous to coat oral solid dosage forms with an enteric or delayed-release coating. This may be accomplished by standard aqueous or nonaqueous techniques. Oral dosage forms suitable for hydroxylansoprazole are described in U.S. Pat. Nos. 5,035,899 and 5,045,321 and in PCT applications WO96/01624, WO97/12580 and WO97/25030.

In addition to the common dosage forms set out above, the compounds of the present invention may also be administered by sustained or controlled release formulations, which are well known in the art. Compositions suitable for rectal administration are described in European Application 645140.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent. Desirably, each tablet or capsule contains about 100–500 mg of the active ingredient.

An enteric coating, such as the polyacrylate Eudragit L® and Eudragit S® series, is applied, preferably with an aqueous dispersion of the coating polymer. Tablets of other strengths may be prepared by altering the ratio of active ingredient to the excipients or to the final weight of the tablet.

The invention is further defined by reference to the following examples describing in detail the preparation of the compositions of the present invention. It will be apparent to those skilled in the art that many modifications, both to materials and methods, may be practiced without departing from the invention.

EXAMPLES

Example 1–250 mg Tablets

| Composition per tablet: | |
|---|---|
| hydroxylansoprazole | 250 mg |
| croscarmellose | 60 mg |
| colloidal silicon dioxide | 8 mg |
| magnesium stearate | 1 mg |
| microcrystalline cellulose | 190 mg |
| croscarmellose | 15 mg |
| talc | 10 mg |
| Total | 534 mg |

Example 1

Hydroxylansoprazole and silicon dioxide are dry mixed, the first portion of croscarmellose is added and the mixture is further dry mixed. The magnesium stearate is added, dry mixed and the mixture is run through a roller compactor and mill. The resulting dry granulate is mixed with the remaining three ingredients and compressed into tablets.

Example 2–200 mg Tablets

| Composition per unit dosage: | |
| --- | --- |
| hydroxylansoprazole | 200 mg |
| pregelatinized starch | 200 mg |
| microcrystalline cellulose | 25 mg |
| povidone | 15 mg |
| croscarmellose | 10 mg |
| magnesium stearate | 3.75 mg |
| FD&C yellow #2 lake | 2.5 mg |
| Water | (5 mL) |
| Total | 456.25 mg |

Example 2

The ingredients above are mixed well in the proportions shown in a high shear mixer until uniform granules result. The mixture is tray-dried at 40EC under vacuum until the desired consistency is reached. The granules are milled to less than 60 mesh using a screen mill and compressed into tablets.

Example 3—Enteric Coating

Enteric Coating Composition

| | |
| --- | --- |
| Eudragit L-30D | 138 mg (solids 41.4 mg) |
| Talc | 4.1 mg |
| Polyethylene glycol 5000 | 12.4 mg |
| Tween 80 | 2.1 mg |
| Water | 250 µl |

Enteric tablets are produced in a pan coater by coating the tablets obtained in Example 2 with the enteric coating composition shown.

What is claimed is:

1. A method of treating a condition chosen from ulcers, Zollinger-Ellison Syndrome, and gastroesophageal reflux disease, said method comprising administering to a human a therapeutically effective amount of hydroxylansoprazole or a pharmaceutically acceptable salt thereof.

2. A method according to claim 1 of treating ulcers which comprises administering to a human a therapeutically effective amount of hydroxylansoprazole or a pharmaceutically acceptable salt thereof.

3. A method according to claim 1 of treating gastroesophageal reflux disease which comprises administering to a human a therapeutically effective amount of hydroxylansoprazole or a pharmaceutically acceptable salt thereof.

4. The method according to claim 1 wherein said condition is Zollinger-Ellison Syndrome.

5. The method of claim 1 wherein racemic hydroxylansoprazole is administered.

6. The method of claim 5 wherein the amount of racemic hydroxylansoprazole or a pharmaceutically acceptable salt thereof administered is from about 50 mg to about 1500 mg per day.

7. The method of claim 5 wherein racemic hydroxylansoprazole is administered orally.

8. The method of claim 1 wherein optically pure (+)-hydroxylansoprazole is administered.

9. The method of claim 8 wherein the amount of (+)-hydrxylansoprazole or a pharmaceutically acceptable salt thereof administered is from about 50 mg to about 1000 mg per day.

10. The method of claim 8 wherein optically pure (+)-hydroxylansoprazole is administered orally.

11. The method of claim 1 wherein optically pure (−)-hydroxylansoprazole is administered.

12. The method of claim 11 wherein the amount of (−)-hydroxylansoprazole or a pharmaceutically acceptable salt thereof administered is from about 50 mg to about 1000 mg per day.

13. The method of claim 11 wherein optically pure (−)-hydroxylansoprazole is administered orally.

\* \* \* \* \*